(12) United States Patent
Stigall et al.

(10) Patent No.: US 8,936,553 B2
(45) Date of Patent: Jan. 20, 2015

(54) DEVICES, SYSTEMS, AND METHODS FOR VISUALIZING AN OCCLUDED VESSEL

(71) Applicant: Volcano Corporation, San Diego, CA (US)

(72) Inventors: Jeremy Stigall, Carlsbad, CA (US); Maritess Minas, San Diego, CA (US)

(73) Assignee: Volcano Corporation, San Diego, CA (US)

( * ) Notice: Subject to any disclaimer, the term of this patent is extended or adjusted under 35 U.S.C. 154(b) by 0 days.

(21) Appl. No.: 13/706,015

(22) Filed: Dec. 5, 2012

(65) Prior Publication Data

US 2013/0150716 A1 Jun. 13, 2013

Related U.S. Application Data

(60) Provisional application No. 61/568,498, filed on Dec. 8, 2011.

(51) Int. Cl.
| | | |
|---|---|---|
| *A61B 8/00* | (2006.01) | |
| *A61B 6/00* | (2006.01) | |
| *A61B 17/22* | (2006.01) | |
| *A61B 8/12* | (2006.01) | |
| *A61B 8/08* | (2006.01) | |
| *A61B 17/3207* | (2006.01) | |
| *A61B 19/00* | (2006.01) | |

(52) U.S. Cl.
CPC ................. *A61B 6/504* (2013.01); *A61B 17/22* (2013.01); *A61B 8/12* (2013.01); *A61B 8/0891* (2013.01); *A61B 17/3207* (2013.01); *A61B 2017/22094* (2013.01); *A61B 2019/528* (2013.01); *A61B 8/4272* (2013.01)
USPC ............................ 600/439; 600/407; 600/459

(58) Field of Classification Search
USPC ......... 600/407, 439, 459, 462–464, 466–467, 600/478
See application file for complete search history.

(56) References Cited

U.S. PATENT DOCUMENTS

| | | | | |
|---|---|---|---|---|
| 5,501,227 A | * | 3/1996 | Yock | 600/463 |
| 6,135,997 A | | 10/2000 | Laufer et al. | |
| 6,266,550 B1 | | 7/2001 | Selmon et al. | |
| 6,457,365 B1 | * | 10/2002 | Stephens et al. | 600/463 |
| 2007/0167804 A1 | * | 7/2007 | Park et al. | 600/459 |
| 2009/0030312 A1 | | 1/2009 | Hadjicostis | |
| 2009/0163818 A1 | | 6/2009 | Zelenka et al. | |
| 2010/0004531 A1 | | 1/2010 | Passmore | |

OTHER PUBLICATIONS

International Search Report and Written Opinion received in Patent Cooperation Treaty Application No. PCT/US2012/067938, dated Mar. 29, 2013, 12 pages.

* cited by examiner

*Primary Examiner* — Peter Luong
(74) *Attorney, Agent, or Firm* — Haynes and Boone, LLP

(57) ABSTRACT

Embodiments of the present disclosure are configured to visualize severe blockages in a vessel and, in particular, chronic total occlusions in blood vessels. In some particular embodiments, the devices, systems, and methods of the present disclosure are configured to visualize the blockage to facilitate safe crossing of the blockage.

22 Claims, 5 Drawing Sheets

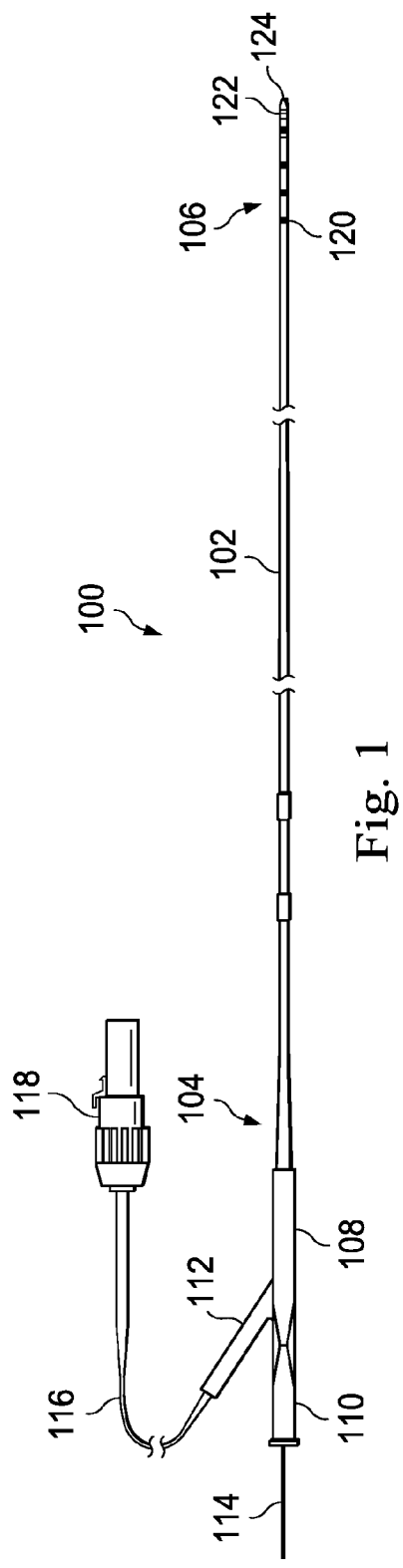
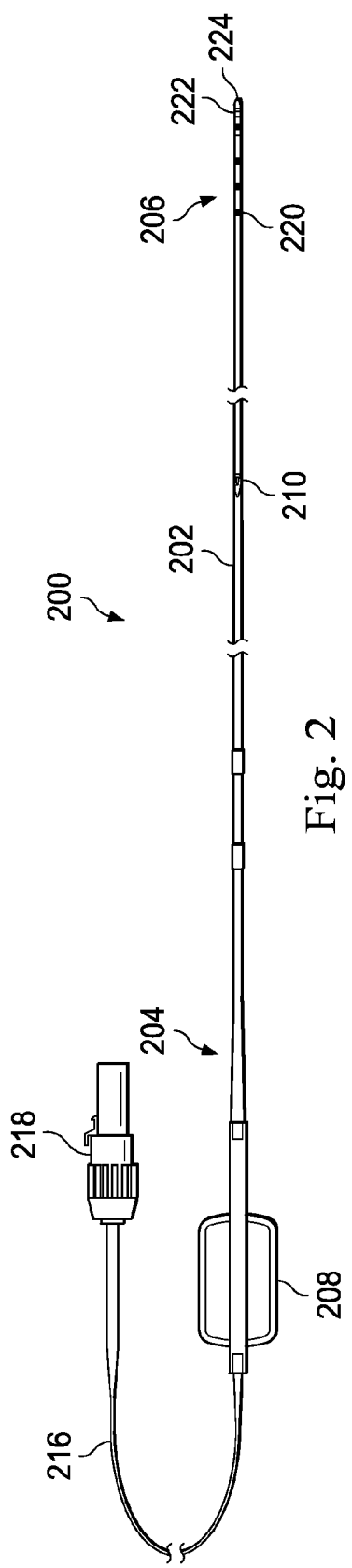

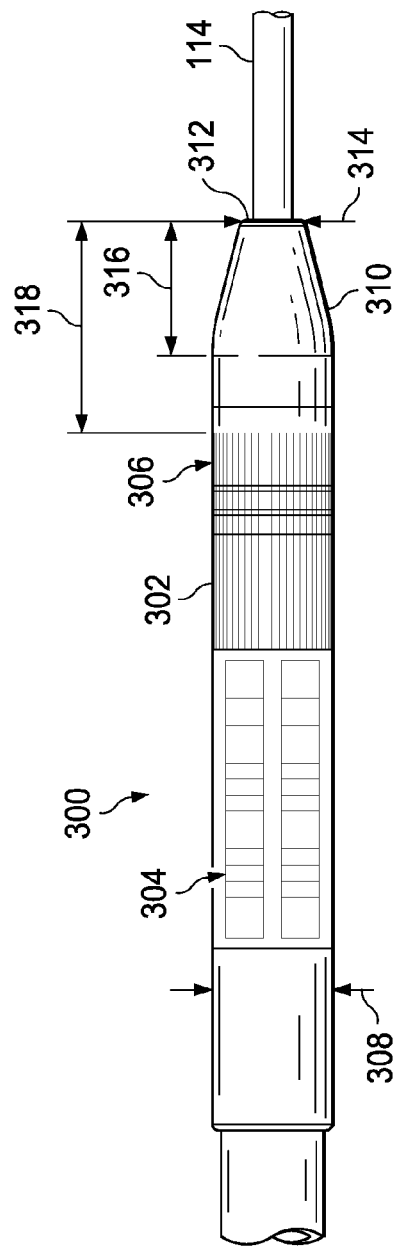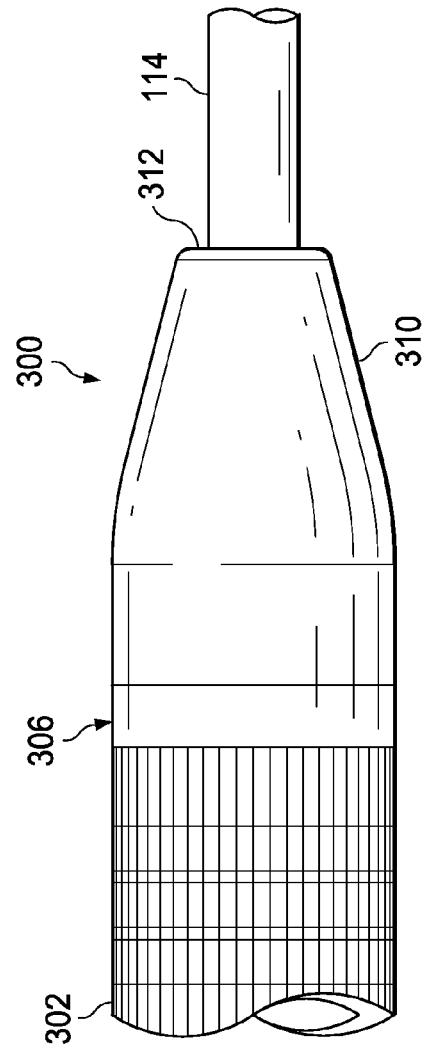
Fig. 3
Fig. 4

DEVICES, SYSTEMS, AND METHODS FOR VISUALIZING AN OCCLUDED VESSEL

CROSS-REFERENCE TO RELATED APPLICATIONS

The present application claims priority to and the benefit of U.S. Provisional Patent Application No. 61/568,498, filed Dec. 8, 2011, which is hereby incorporated by reference in its entirety.

TECHNICAL FIELD

The present disclosure relates generally to the visualization of vessels and, in particular, the visualization of vessels having a blockage or other restriction to the flow of fluid through the vessel. Aspects of the present disclosure are particularly suited for evaluation of biological vessels in some instances. For example, some particular embodiments of the present disclosure are specifically configured for the visualizing and treating total occlusions of human blood vessels, such as a chronic total occlusion, an acute total occlusion, or a severe stenosis.

BACKGROUND

Intravascular ultrasound (IVUS) imaging systems have been designed for use by interventional cardiologists in the diagnosis and treatment of cardiovascular and peripheral vascular disease. Such systems enhance the effectiveness of the diagnosis and treatment by providing important diagnostic information that is not available from conventional x-ray angiography. This information includes the location, amount, and composition of arteriosclerotic plaque and enables physicians to identify lesion characteristics, select an optimum course of treatment, position therapeutic devices and promptly assess the results of treatment.

Such IVUS systems generally include an IVUS device having one or more miniaturized transducers mounted on the distal portion of a catheter or guide wire to provide electronic signals to an external imaging system. The external imaging system produces an image of the lumen of the artery or other cavity into which the catheter is inserted, the tissue of the vessel, and/or the tissue surrounding the vessel. Problems encountered with these systems include clearly visualizing the tissue around the catheter, and identifying the precise location of the image with regard to known spatial references, such as angiographic references.

Before the development of less invasive approaches, the principal mode of treatment for occluded arteries was bypass surgery and, in the case of occlusions in the coronary arteries, coronary artery bypass surgery. Coronary artery bypass surgery is a highly invasive procedure in which the chest cavity is opened to expose the heart to provide direct surgical access to the coronary arteries. The procedure also includes the surgical removal of blood vessels from other locations in the patient's body (e.g., the sapheneous vein) which then are grafted surgically to the coronary arteries to bypass the occlusions. The recuperative period is lengthy with considerable discomfort to the patient.

The use of less invasive, catheter-based, intravascular techniques has developed for several decades and may be considered as the preferred mode of treatment for those patients amenable to such treatment. Typically, the intravascular procedures, such as angioplasty, atherectomy, and stenting require preliminary navigation of a guidewire through the patient's arteries to and through the occlusion. This guidewire, so placed, serves as a rail along which catheters can be advanced directly to and withdrawn from the target site. Total occlusions often cannot be treated with such minimally invasive intravascular approaches because of the inability to advance a guidewire through the stenosis. Typically patients with such occlusions have been treatable, if at all, by bypass surgery. Although in some instances, physicians may be able to force a guidewire through a total occlusion if the occluding material is relatively soft, attempts to force the guidewire through can present serious risks of perforating the artery. Arterial perforation can be life threatening.

The difficulties presented when trying to cross a total or near-total occlusion are compounded by the typical manner in which the anatomy of an occluded artery is diagnosed. Conventionally, such diagnosis involves an angiographic procedure in which a radiopaque contrast liquid is injected into the artery upstream of the occlusion and a radiographic image is made. The resulting image is that of the compromised lumen which necessarily differs from the natural arterial lumen. Although with angiographic visualization techniques, the physician can determine the location of the occluded region and an indication of the degree of obstruction, angiographic images do not provide a clear understanding of where, in the occluded region, the natural boundaries of the vessel are located.

As used herein, the term "severe occlusion" or "severe obstruction" is intended to include total occlusions as well as those occlusions and stenoses that are so restrictive as to require preliminary formation of a passage through the occlusion in order to receive additional intravascular therapeutic devices. Such occlusions have various causes and occur in both the arterial or venous systems. Total or near total occlusions occur in some instances as a consequence of the buildup of plaque or thrombus, the latter being problematic in arteries as well as in the venous system. For example, deep veined thrombus and thrombotic occlusion of vein grafts are serious conditions requiring treatment.

As noted above, recently techniques and systems have been developed to visualize the anatomy of vascular occlusions by using intravascular ultrasound (IVUS) imaging. IVUS techniques are catheter-based and provide a real-time sectional image of the arterial lumen and the arterial wall. An IVUS catheter includes one or more ultrasound transducers at the distal portion of the catheter by which images containing cross-sectional information of the artery under investigation can be determined. The ultrasound transducer(s) are typically spaced from the distal tip of the catheter. In that regard, the catheters typically include a distal tip formed of a radiopaque material such that the distal tip of the catheter is identifiable on fluoroscopy, x-ray, angiograph, or other similar imaging techniques. As a result of the distal tip, the ultrasound transducer(s) may be anywhere from one to five centimeters proximal of the distal tip of the catheter. For example, in each of the Atlantis SR Pro Imaging Catheter and iCross Coronary Imaging Catheter available from Boston Scientific Corporation, the ultrasound transducer is positioned 2.1 cm proximal of a marker band near the distal tip such that the ultrasound transducer is approximately 3 cm proximal of the distal tip of the device. Further, even in the EagleEye® Platinum RX Digital IVUS Catheter available from Volcano Corporation, the transducer array is spaced from the distal tip by a distance of 1 cm. This spacing of the ultrasound transducer(s) from the distal tip of the device is suitable for many vessel visualization applications and evaluations, but has limited effectiveness in the visualization and evaluation of severe occlusions Accordingly, there remains a need for improved devices, systems, and methods for visualizing vessels having a severe blockage or other restriction to the flow of fluid through the vessel. In that regard, there remains a need for improved devices, systems, and methods for visualizing the severe blockage to facilitate safely crossing the blockage.

SUMMARY

Embodiments of the present disclosure are configured to visualize a blockage in a vessel and, in particular, a severe blockage in a blood vessel to facilitate crossing of that blockage. In some instances, devices particularly suited for visualizing a blockage are provided. In that regard, the devices include one or more imaging elements (such as ultrasound, OCT, thermal, and/or other imaging modality) positioned adjacent the distal tip of the device. In some instances, the imaging element(s) are positioned less than 5 mm, less than 4 mm, less than 3 mm, less than 2 mm, less than 1 mm, and/or less than 0.5 mm from the distal tip of the device. Further, in some implementations the device is a catheter that includes an inner lumen that is sized and shaped to receive a guidewire. In that regard, in some embodiments the catheter is arranged as a rapid-exchange catheter having at least one opening in communication with the central lumen for receiving the guidewire, the opening being positioned between the proximal and distal ends of the catheter. In other embodiments, the catheter is an over-the-wire catheter.

In other instances, methods of crossing a total occlusion of a vessel of a patient are provided. The method includes introducing an imaging device into the vessel of the patient, advancing the imaging device to a position immediately adjacent the total occlusion of the vessel such that a distal tip of the imaging device is in contact with the occlusion and one or more imaging elements (such as ultrasound, OCT, thermal, and/or other imaging modality) of the imaging device are positioned less than 5 mm, less than 4 mm, less than 3 mm, less than 2 mm, less than 1 mm, and/or less than 0.5 mm from the occlusion. The method further includes obtaining images of the vessel, including the occlusion, with the imaging device positioned immediately adjacent the total occlusion. In some instances, the method further includes penetrating the total occlusion based on the images obtained by the imaging device. In that regard, in some instances an ablation guidewire or other occlusion crossing device is advanced through a central lumen of the imaging device to the occlusion. In some instances, the occlusion is partially penetrated or crossed using the ablation guidewire (e.g., RF, laser, electric, plasma, etc.) or other occlusion crossing device (e.g., needle, etc.), then the imaging device is advanced into the opening created by the partial penetration/crossing and again used to image the vessel, including the occlusion. This process can be repeated to safely guide the ablation guidewire or other occlusion crossing device through the occlusion.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 1 is a diagrammatic perspective view of an imaging device according to an embodiment of the present disclosure.

FIG. 2 is a diagrammatic perspective view of an imaging device according to another embodiment of the present disclosure.

FIG. 3 is a diagrammatic side view of a distal portion of an imaging device, such as the imaging devices shown in FIGS. 1 and 2, according to an embodiment of the present disclosure.

FIG. 4 is a close up diagrammatic side view of a distal tip of the distal portion of the imaging device shown in FIG. 3.

DETAILED DESCRIPTION

Figure 5:
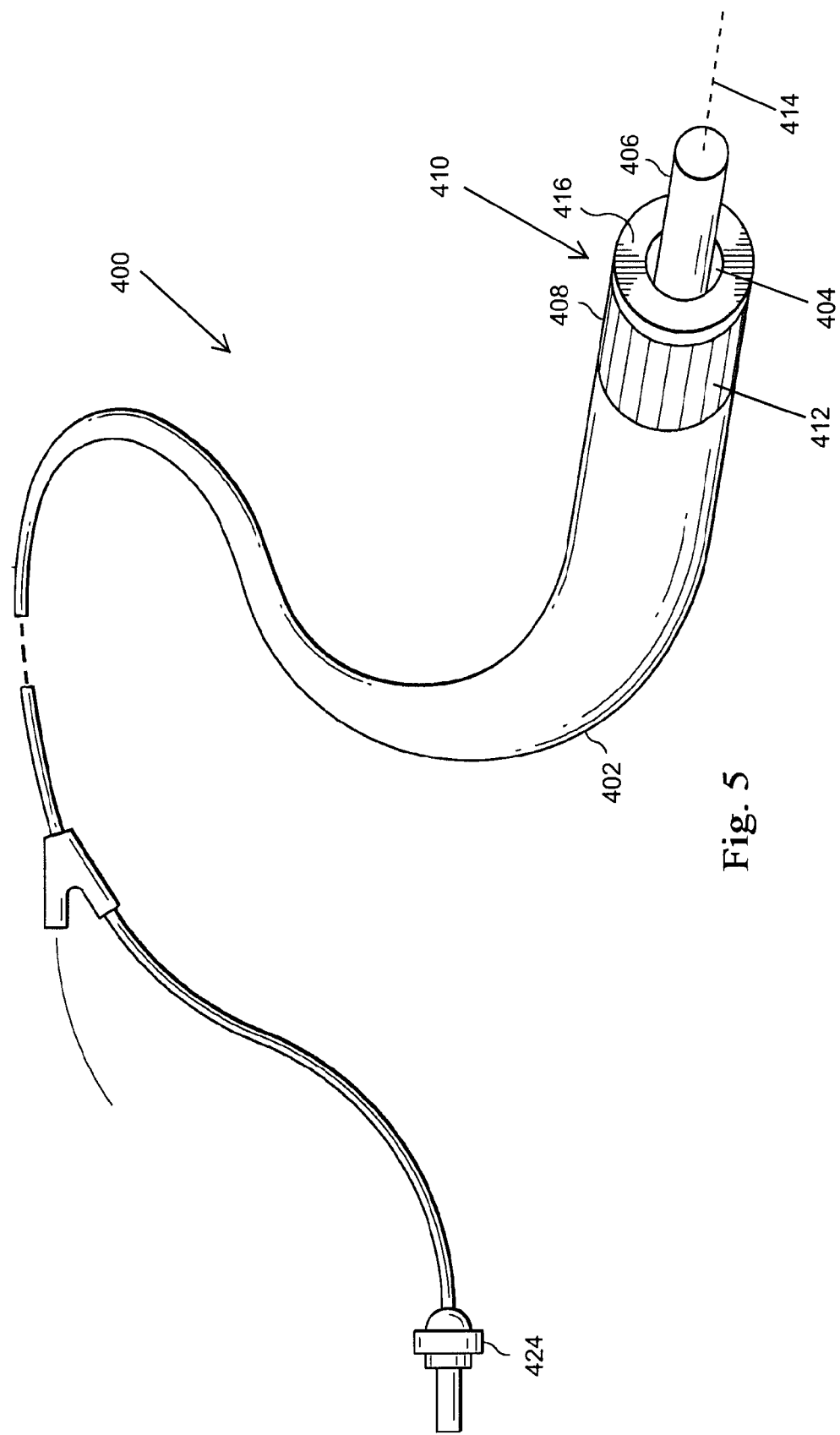
FIG. 5 is a diagrammatic perspective view of an imaging system according to an embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Referring to FIG. 1, shown therein is an imaging device 100 according to an embodiment of the present disclosure. As shown, the imaging device 100 comprises an elongate flexible body 102 having a proximal portion 104 and a distal portion 106. The proximal portion 104 includes an adapter 108. In the illustrated embodiment, the adapter 108 is y-shaped with extensions 110 and 112. In that regard, extension 110 generally extends along the longitudinal axis of the body 102, while extension 112 extends at an oblique angle with respect to the longitudinal axis of the body. Generally, the extensions 110 and 112 provide access to the body 102. In that regard, in the illustrated embodiment extension 110 is configured to receive a guidewire 114 that is sized and shaped to fit within a lumen that extends along the length of the body 102 from the proximal portion 104 to the distal portion 106 and defines an opening at the distal end of the imaging device 100. As a result of this arrangement, the imaging device 100 is understood to be what is commonly referred to as an over-the-wire catheter. In some embodiments, the lumen of the imaging device is centered about the central longitudinal axis of the body 102. In other embodiments, the lumen is offset with respect to the central longitudinal axis of the body 102.

In the illustrated embodiment, extension 112 of adapter 108 is configured to receive communication lines (e.g., electrical, optical, and/or combinations thereof) that are coupled to imaging components positioned within the distal portion 106 of the imaging device 100. In that regard, a cable 116 containing one or more communication lines extends from extension 112 to a connector 118. The connector 118 is configured to interface the imaging device directly or indirectly with one or more of a patient interface module ("PIM"), a processor, a controller, and/or combinations thereof. The particular type of connection depends on the type of imaging components implemented in the imaging device, but generally include one or more of an electrical connection, an optical connection, and/or combinations thereof.

The distal portion 106 includes a plurality of markers 120. In that regard, the markers 120 are visible using non-invasive imaging techniques (e.g., fluoroscopy, x-ray, CT scan, etc.) to track the location of the distal portion 106 of the imaging device 100 within a patient. Accordingly, in some instances the markers 120 are radiopaque bands extending around the circumference of the body 102. Further, the markers 120 are positioned at known, fixed distances from an imaging element 122 and/or the distal end 124 of the imaging device 100 in some instances. While the distal portion 106 has been illustrated and described as having a plurality (two or more) of markers 120, in other embodiments the distal portion 106 includes one marker or no markers. Further, in some embodiments, one or more components associated with the imaging element 122 can be utilized as a marker to provide a reference of the position of the distal portion 106 of the imaging device 100.

The imaging element 122 may be any type of imaging element suitable for visualizing a vessel and, in particular, a sever occlusion in a vessel. Accordingly, the imaging element may be an ultrasound transducer array (e.g., arrays having 16, 32, 64, or 128 elements are utilized in some embodiments), a single ultrasound transducer, one or more optical coherence tomography ("OCT") elements (e.g., mirror, reflector, and/or optical fiber), and/or combinations thereof. In that regard, in some embodiments the imaging device 100 is configured to be rotated (either manually by hand or by use of a motor or other rotary device) to obtain images of the vessel.

Referring to FIG. 2, shown therein is an imaging device 200 according to another embodiment of the present disclosure. As shown, the imaging device 200 comprises an elongate flexible body 202 having a proximal portion 204 and a distal portion 206. The proximal portion 204 includes a handle 208 for grasping by a user. In the illustrated embodiment, a cable 216 extends from the handle 208 and includes one or more communication lines (e.g., electrical, optical, and/or combinations thereof) that are coupled to imaging components positioned within the distal portion 206 of the imaging device 200. In that regard, a cable 216 containing one or more communication lines extends from handle 208 to a connector 218. The connector 218 is configured to interface the imaging device directly or indirectly with one or more of a patient interface module ("PIM"), a processor, a controller, and/or combinations thereof. The particular type of connection depends on the type of imaging components implemented in the imaging device, but generally include one or more of an electrical connection, an optical connection, and/or combinations thereof.

The body 202 includes an opening 210 that is in communication with a lumen that extends along the length of the body 202 from the opening 210 to the distal portion 206 and defines an opening at the distal end of the imaging device 200. The opening 210 and the lumen it is in communication with are configured to receive a guidewire. As a result of this arrangement, the imaging device 200 is understood to be what is commonly referred to as a rapid exchange catheter. In some embodiments, the lumen of the imaging device is centered about the central longitudinal axis of the body 202. In other embodiments, the lumen is offset with respect to the central longitudinal axis of the body 202.

The distal portion 206 includes a plurality of markers 220. In that regard, the markers 220 are visible using non-invasive imaging techniques (e.g., fluoroscopy, x-ray, CT scan, etc.) to track the location of the distal portion 206 of the imaging device 200 within a patient. Accordingly, in some instances the markers 220 are radiopaque bands extending around the circumference of the body 202. Further, the markers 220 are positioned at known, fixed distances from an imaging element 222 and/or the distal end 224 of the imaging device 200 in some instances. While the distal portion 106 has been illustrated and described as having a plurality (two or more) of markers 220, in other embodiments the distal portion 206 includes one marker or no markers. Further, in some embodiments, one or more components associated with the imaging element 222 can be utilized as a marker to provide a reference of the position of the distal portion 206 of the imaging device 200.

The imaging element 222 may be any type of imaging element suitable for visualizing a vessel and, in particular, a sever occlusion in a vessel. Accordingly, the imaging element may be an ultrasound transducer array (e.g., arrays having 16, 32, 64, or 128 elements are utilized in some embodiments), a single ultrasound transducer, one or more optical coherence tomography ("OCT") elements (e.g., mirror, reflector, and/or optical fiber), and/or combinations thereof. In that regard, in some embodiments the imaging device 200 is configured to be rotated (either manually by hand or by use of a motor or other rotary device) to obtain images of the vessel.

Referring now to FIGS. 3 and 4, shown therein is a distal portion 300 of an imaging device according to an embodiment of the present disclosure. In that regard, the illustrated arrangement of the distal portion 300 is suitable for use in both over-the-wire catheters (e.g., imaging device 100 of FIG. 1) and rapid exchange catheters (e.g., imaging device 200 of FIG. 2). As shown, the distal portion 300 includes a main body 302 the contains imaging components 304, which may include various electronic, optical, and/or electro-optical components necessary for the particular imaging modality utilized by the imaging device. In the illustrated embodiment, the distal portion 300 of the imaging device is configured for ultrasound imaging and includes an array 306 of ultrasound transducers arranged circumferentially about the distal portion 300 of the imaging device. In that regard, in some embodiments the transducer array 306 and associated components 304 include features as disclosed in U.S. Pat. No. 5,857,974 to Eberle et al. that issued Jan. 12, 1999, U.S. Pat. No. 6,283,921 to Nix et al. that issued on Sep. 4, 2001, U.S. Pat. No. 6,080,109 to Baker et al. that issued on Jun. 27, 2000, U.S. Pat. No. 6,123,673 to Eberle et al. that issued on Sep. 26, 2000, U.S. Pat. No. 6,457,365 to Stephens et al. that issued on Oct. 1, 2002, U.S. Pat. No. 7,762,954 to Nix et al. that issued on Jul. 27, 2010, U.S. Pat. No. 7,846,101 to Eberle et al. that issued on Dec. 7, 2010, and U.S. Patent Application Publication No. 2004/0054287 that published on Mar. 18, 2004, each of which is hereby incorporated by reference in its entirety.

As shown, the main body 302 of the distal portion 300 has a diameter or thickness 308. Generally, the diameter or thickness 308 of the distal portion 300 closely matches the diameter of the main body of the imaging device. In some instances, the diameter or thickness 308 of the distal portion 300 exactly matches the diameter of the main body of the imaging device. In other instances, the diameter or thickness 308 of the distal portion 300 is slightly larger or slight smaller than the diameter of the main body of the imaging device. In some instances, the diameter or thickness 308 is between about 0.5 mm and about 5 mm, with some particular embodiments having a diameter or thickness of 2.73 mm (8.2 French), 2.33 mm (7 French), 1.17 mm (3.5 French), 1.1 mm (3.3 French), 1.0 mm (3 French), 0.97 mm (2.9 French), or otherwise.

The distal portion 300 also includes a tapered tip portion 310 that extends distally from the main body 302 to the distal end 312. As shown, the tapered tip portion 310 transitions the distal portion 300 from the diameter or thickness 308 to a reduced diameter or thickness 314 at the distal end 312. In some instances, the diameter or thickness 314 is between about 0.30 mm and about 2.5 mm, with some particular embodiments having a diameter or thickness of 0.30 mm (0.012" or 0.9 French), 0.38 mm (0.015" or 1.14 French), 0.48 mm (0.019" or 1.44 French), or otherwise. In that regard, the diameter or thickness 314 is determined based on the desired lumen size for the imaging device in some instances. For example, as shown in FIGS. 3 and 4 a guidewire 114 is received within the lumen of the imaging device such that it extends through an opening in the distal end 312 of the imaging device. In some particular instances, the guidewire 114 has an outer diameter between about 0.28 mm (0.011" or 0.84 French) and about 0.46 mm (0.018" or 1.38 French) mm, with some embodiments having an outer diameter of 0.36 mm (0.014" or 1.07 French). In other instances, the guidewire 114 has outer diameter outside of this range, either larger or smaller. As the distal end 312 of the imaging device defines the opening that receives the guidewire, the diameter or thickness 314 is between 0.28 mm (0.011" or 0.84 French) and about 0.5 mm (0.020" or 1.5 French) in some embodiments. In that regard, it is understood that the distal end 312 of the imaging device will necessarily have a slightly larger diameter or thickness than that of the guidewire 114 such that the guidewire can be received therein. However, in some instances the diameter or thickness 314 of the distal end 312 of the imaging device is within 0.03 mm (0.001" or 0.09 French) or less of the outer diameter of the guidewire. In other instances, the diameter or thickness 314 of the distal end 312 of the imaging device is within 0.5 mm (0.020" or 1.5 French) or less of the outer diameter of the guidewire.

As shown, the tapered tip portion 310 of the imaging device extends proximal of the distal end 312 by a distance 316. In that regard, the distance 316 is less than 5 mm in some embodiments. Further, the distance 316 is less than 4 mm, less than 3 mm, less than 2 mm, less than 1 mm, and/or less than 0.5 mm from the distal end 312 of the device in some instances. The distance 316 and the difference between the diameter or thickness 308 of the main body 302 and the diameter or thickness 314 at the distal end 312 determine the slope of the outer surface defined by the tapered tip portion 310. In that regard, in some embodiments the tapered tip portion 310 includes a constant taper between the diameter or thickness 308 of the main body 302 at the proximal end of the tapered tip portion and the diameter or thickness 314 at the distal end 312 of the tapered tip portion. In other instances, the tapered tip portion 310 includes a variable taper between the diameter or thickness 308 of the main body 302 at the proximal end of the tapered tip portion and the diameter or thickness 314 at the distal end 312 of the tapered tip portion. For example, in some instances the degree of taper decreases as the tapered tip portion 310 extends distally towards the distal end 312.

Referring now to FIG. 5, there is shown a catheter 400 for intravascular use, which may be similar to either of imaging devices 100 and 200 discussed above. In that regard, this catheter has an elongated flexible body 402 with an axially extending lumen 404 through which a guide wire 406, fluids, and/or various therapeutic devices or other instruments can be passed. The present disclosure is not, however, limited to use with the illustrated catheter arrangements, and it can be utilized with any suitable catheter, guide wire, probe, etc. An ultrasonic imaging transducer assembly 408 is provided at the distal portion 410 of the catheter, with a connector 424 located at the proximal end of the catheter. This transducer 408 comprises a plurality of transducer elements 412 that are preferably arranged in a cylindrical array centered about the longitudinal axis 414 of the catheter for transmitting and receiving ultrasonic energy. The transducer elements 412 are mounted on a cylindrical substrate 416 which, in the embodiment illustrated, consists of a flexible circuit material that has been rolled into the form of a tube. A transducer backing material with the proper acoustical properties surrounds the transducer elements 412.

Each of the transducer elements 412 comprises an elongated body of PZT or other suitable piezoelectric material. The elements extend longitudinally on the cylindrical substrate and parallel to the axis of the catheter. Each element has a rectangular cross-section, with a generally flat surface at the distal end thereof. The transducer elements are piezoelectrically poled in one direction along their entire length as highlighted. In some embodiments, a transversely extending notch of generally triangular cross-section is formed in each of the transducer elements. The notch opens through the inner surface of the transducer element and extends almost all the way through to the outer surface. Preferably, the notch has a vertical sidewall on the distal side and an inclined sidewall on the proximal side. The vertical wall is perpendicular to the longitudinal axis of the catheter, and the inclined wall is inclined at an angle on the order of 60 degrees to the axis. The notch, which exists in all the array transducer elements, can be filled with a stable non-conductive material. An example of a material that can be used to fill notch is a non-conductive epoxy having low acoustic impedance. Although not the preferred material, conductive materials having low acoustic impedance may also be used to fill notch. If a conductive material is used as the notch filler, it could avoid having to metalize the top portion to interconnect both portions of the transducer elements as required if a nonconductive material is utilized. Conductive materials are not the preferred notch filler given that they have an affect on the E-fields generated by the transducer elements.

In the preferred embodiment, the transducer array provides for a forward looking elevation aperture for 10 mega Hertz (MHz) ultrasound transmit and receive, and a side looking elevation aperture for 20 MHz ultrasound transmit and receive. Other frequencies and/or frequency combinations can be used depending on the particular design requirements or intended uses for the imaging device. The transducer array is manufactured by electrically and mechanically bonding a poled, metalized block of the piezoelectric material to the flexible circuit substrate with the substrate in its unrolled or flat condition. The transducer block exists, as a piezoelectrically poled state where the thickness-axis poling is generally uniform in distribution and in the same axis throughout the entire block of material. If included, a notch is then formed across the entire piezoelectric block, e.g. by cutting it with a dicing saw. Each of the individual notches is filled with a material such as plastic and a metallization is applied to the top of the notch to form a continuous transducer inner electrode with metallization. The block is then cut lengthwise to form the individual elements that are isolated from each other both electrically and mechanically, with kerfs formed between the elements. Cable wire attachment terminals are provided on the substrate that allow microcables that are electrically connected to an external ultrasound system to connect with the transducer assembly in order to control the transducers.

Integrated circuits are installed on the substrate and the substrate is then rolled into its cylindrical shape, with the transducer elements on the inner side of the cylinder. The sleeve of radiopaque material is mounted on the core, the core is positioned within the cylinder, and the acoustic absorbing material is introduced into the volume between the core and the transducer elements. In the event that a radiopaque marker is not required for a particular application, it can be omitted. The transducer elements 412 can be operated to preferentially transmit and receive ultrasonic energy in either a thickness extensional TE) mode ($k_{33}$ operation) or a length extensional (LE) mode ($k_{31}$ operation). The frequency of excitation for the TE mode is determined by the thickness of the transducer elements in the radial direction, and the frequency for the LE mode is determined by the length of the body between distal end surface and the vertical wall of notch. The thickness TE mode is resonant at a frequency whose half wavelength in the piezoelectric material is equal to the thickness of the element. And the LE mode is resonant at a frequency whose half wavelength in the piezoelectric material is equal to the distance between the distal end and the notch. Each transducer element is capable of individually operating to transmit and receive ultrasound energy in either mode, with the selection of the desired mode (i.e. "side", or "forward") being dependent upon; a) an electronically selected frequency band of interest, b) a transducer design that spatially isolates the echo beam patterns between the two modes, and c) image plane specific beam-forming weights and delays for a particular desired image plane to reconstruct using synthetic aperture beam-forming techniques, where echo timing incoherence between the "side" and "forward" beam patterns will help maintain modal isolation.

Figure 7:
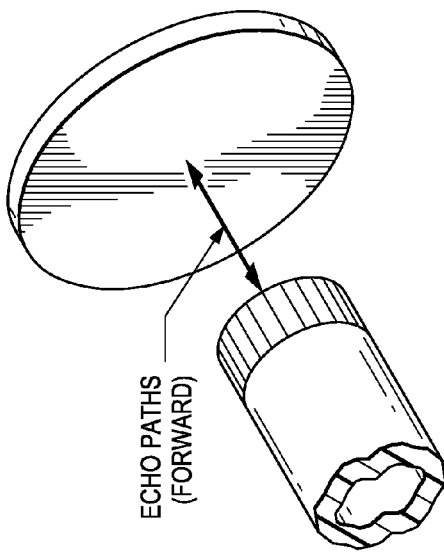
FIG. 7 is an isometric view of a forward-looking imaging plane of an imaging device according to an embodiment of the present disclosure.
Figure 8:
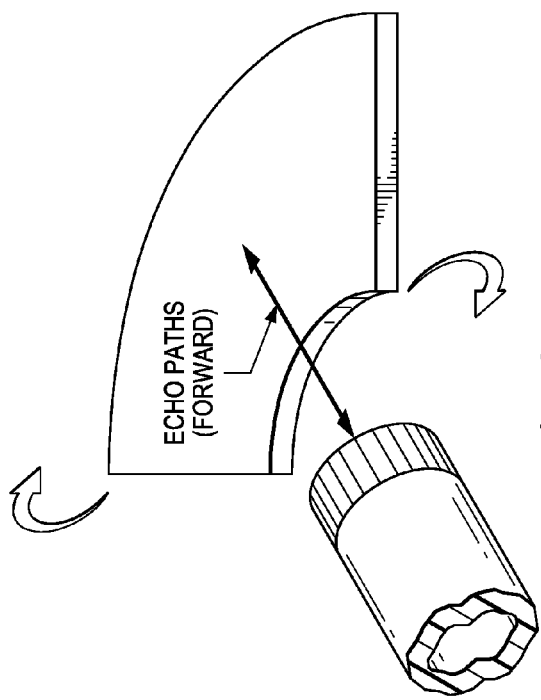
FIG. 8 is an isometric view of a forward-looking imaging plane of an imaging device according to another embodiment of the present disclosure.
Figure 6:
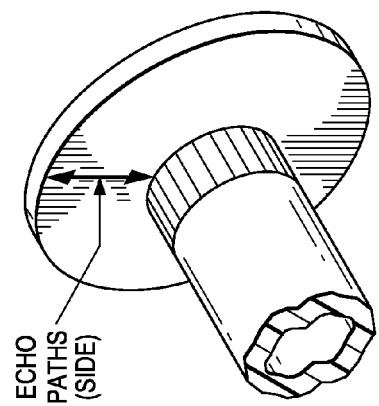
FIG. 6 is an isometric view of a side-looking or lateral imaging plane of an imaging device according to an embodiment of the present disclosure.

Referring now to FIGS. 6-8, shown therein are various imaging planes that are utilized in some embodiments of the devices and methods of the present disclosure. In that regard, some of the ultrasonic imaging catheters of the present disclosure are configured to be "side looking" devices that produce B-mode images in a plane that is perpendicular to the longitudinal axis of the catheter and passes through the transducer. That plane can be referred to as the B-mode lateral plane and is illustrated in FIG. 6. Further, some of the ultrasonic imaging catheters of the present disclosure are configured to be "forward looking" devices that produce a C-mode image plane that is perpendicular to the axis of the catheter and spaced distally from the transducer array, which is illustrated in FIG. 7. Further still, some of the ultrasonic imaging catheters of the present disclosure are configured to be "forward looking" devices that produce a B-mode image in a plane that extends in a forward direction from the transducer and parallel to the axis of the catheter. That imaging plane is referred to as the B-mode forward plane and is illustrated in FIG. 8. Forward viewing devices can be particularly advantageous in some crossing severe occlusions as they allow the physician to see aspects of the occlusion in front of the catheter. Finally, some of the ultrasonic imaging catheters of the present disclosure are configured to transition between two or more of the imaging planes shown in FIGS. 6-8. The following discusses ways these multiple modes of imaging can be implemented. It is understood that some embodiments of the present disclosure implement only a single one of these imaging modes. Further, it is understood that any suitable operating frequencies may be utilized for the different imaging modes, including frequencies between 10 MHz and 80 MHz, including without limitation 10 MHz, 20 MHz, 40 MHz, and 80 MHz. The forward-looking imaging modes described below utilize a 20 MHz operating frequency in some instances.

Multiple Modes of Imaging: Explanation of the Principals of Operation

A piezoelectric transducer, when properly excited, will perform a translation of electrical energy to mechanical energy, and as well, mechanical to electrical. The effectiveness of these translations depends largely on the fundamental transduction efficiency of the transducer assembly taken as a whole. The transducer is a three dimensional electromechanical device though, and as such is always capable of some degree of electromechanical coupling in all possible resonate modes, with one or several modes dominating. Generally an imaging transducer design seeks to create a single dominate mode of electromechanical coupling, suppressing all other coupling modes as "spurious." The common method used to accomplish a transducer design with a single dominate mode of electromechanical coupling usually rests in the creation of a single, efficient mechanical coupling "port" to the medium outside of the transducer. The single port is created by mounting the transducer such that the most efficient resonant mode of transducer operation faces that mechanical coupling port, with all other modes suppressed by means of mechanical dispersion attained by transducer dimensional control and dampening materials.

In the design of the present disclosure, the transducer design utilizes the fact that a transducer can be effective in two principal electromechanical coupling modes, each mode using a different frequency of operation, acoustic "port", and electro-mechanical coupling efficiency. One port is the "side looking" port that is used in the cross-sectional view image (as shown in FIG. 6). The other port is the "end" or "forward looking" port of the array (as shown in FIGS. 7 and 8).

The present disclosure allows the two electromechanical coupling modes (i.e. "side" and "forward") to be always active, without any mechanical switching necessary to choose one mode exclusive of the other. This design also assures that echoes of any image target in the "side looking" plane (see FIG. 6) do not interfere with the target reconstruction in the "forward looking" planes (see FIGS. 7 and 8), and reciprocally, image targets from the "forward looking" do not interfere with the target reconstruction in the "side looking" planes. In accordance with the disclosure, the design methods listed below are used to maintain sufficient isolation between the two modes of operation.

A) Resonant and Spatial Isolation of the Two Modes

In some instances, the "side looking" port is designed for approximately twice the frequency of the "forward looking" port in accordance with the preferred embodiment. The transducer dimensional design is such that the "high frequency and side looking" transducer port sensitivity to low frequency signals, and as well the "low frequency and forward looking" transducer port to high frequency signals, is very low.

Additionally, the transmit and receive acoustic "beam" directions of the two modes are at approximately right angles to each other and this feature offers an additional isolation with respect to image target identification. Also, as a means to further promote isolation between the two modes of operation, and as well optimize a sparse array echo collection method, the echo collection process in "forward" beam reconstruction uses an intentional physical separation of transmitting and receiving transducer elements of preferably 10 elements or more in the circular array annulus. This physical separation aids in preventing "spurious" transmit echoes from the "high frequency side looking" port from contaminating the receiving element listening to "forward only" echoes at the its lower frequency of operation.

B) Electrical Frequency Band Isolation of the Two Modes

As stated previously, the two modes of operation are operated at center frequencies that differ by about a factor of two. This design feature allows for additional isolation between the two modes through the use of band pass filters in the host system that is processing the echo signals received from the catheter. Additionally, if one or both of the two modes is operated in a low fractional bandwidth design (i.e. <30%), the bandpass filters will be even more effective in the maintenance of very high modal isolation.

C) Beam Formation Isolation Through Synthetic Aperture Reconstruction

Synthetic aperture beam reconstruction is used for all image modes. The beam formation process will preferentially focus only on image targets that are coherently imaged in a particular image plane. Thus, while image reconstruction is forming an image in, for example, the "side looking" plane, targets that may have contaminated the echoes from the "forward looking" planes will be generally incoherent and will be suppressed as a type of background noise. The reciprocal is also true: "side looking" echoes contaminants will be generally incoherent in "forward looking" imaging and will be suppressed through the process of synthetic aperture reconstruction.

A flexible digital image reconstruction system is required for the creation of multiple image planes on demand. The preferred method of assembling multiple image planes utilizes a synthetic aperture reconstruction approach. The "side looking" image shown in FIG. 1 can be reconstructed using sampled transducer element apertures as large as for example 14 contiguous transducer elements in a 64 total transducer element circular array. The transmit-receive echo collection for aperture reconstruction can be continuously shifted around the circular array, sampling all transmit-receive cross-product terms to be used in a particular aperture reconstruction. Within any 14-element aperture there can be 105 independent transmit-receive echo cross products used to construct the image synthetically.

"Forward looking" images shown in FIGS. 7 and 8 can be reconstructed using sampled apertures that consist of selected transducer elements arranged on the annulus end of the circular array. For the 64 transducer element example mentioned above, all elements may contribute to a complete data set capture (this would consist of 64 by 32 independent transmit-receive element cross-products) to form a "forward looking" image in either C-mode or B-mode. As an alternative to the complete data set approach, a reduced number of independent transmit-receive element cross-products are used to adequately formulate the image. The transmit-receive echo collection for aperture reconstruction can be continuously shifted around the circular array, sampling all transmit-receive element cross-products to be used in a particular aperture reconstruction.

Special signal processing may be advantageous, especially in the "forward looking" imaging modes that use a less efficient transducer coupling coefficient ($k_{31}$) and as well may suffer from additional diffraction loss not experienced in the "side looking" mode of synthetic aperture imaging. In forming a "forward looking" C-mode image plane as an example, a low noise bandwidth can be achieved by using a high number of transmit pulses and a narrow bandpass echo filter in the processing system. Additionally, or as a preferred alternative, a matched filter implementation from the use of correlation processing may be used to improve the echo signal-to-noise ratio.

Standard Cross-Sectional B-Mode Operation

The advantage of this cross-sectional B-mode operation of the catheter imaging device is in its ability to see an image at great depth in the radial dimension from the catheter, and at high image resolution. This depth of view can help aid the user of the catheter to position the device correctly prior to electronically switching to a "forward viewing" mode of operation. Image targets moving quickly in a path generally parallel to the long axis of the catheter can be detected and displayed as a colored region in this mode; this information can be used to compare and confirm moving target information from the "forward viewing" mode of operation of the catheter to enhance the usefulness of the imaging tool.

1. Transducer Operation

The transducer in this "primary" mode operates in the thickness extensional (TE) resonance, utilizing the $k_{33}$ electro-mechanical coupling coefficient to describe the coupling efficiency. This "thickness resonance" refers to a quarter wave or half wave (depending on the acoustic impedance of the transducer backing formulation) resonance in the transducer dimension that is in alignment with the polarization direction of the transducer, and also the sensed or applied electric field. This TE mode utilizes a typically high frequency thickness resonance developed in the transducer short dimension following either electric field excitation to generate ultrasound acoustic transmit echoes, or, in reception mode following acoustic excitation to generate an electric field in the transducer.

Array Stepping

The TE mode is used for generating a cross-sectional B-mode image. This cross-section image cuts through the array elements in an orthogonal plane to the long axis of the transducer elements. Echo information gathered from sequential transducer element sampling around the array allows for the synthetically derived apertures of various sizes around the array. For the creation of any synthetically derived aperture, a contiguous group of transducer elements in the array are sequentially used in a way to fully sample all the echo-independent transmit-receive element pairs from the aperture. This sequencing of elements to fully sample an aperture usually involves the transmission of echo information from one or more contiguous elements in the aperture and the reception of echo information on the same or other elements, proceeding until all the echo independent transmit-receive pairs are collected.

Notch Effect

The small notch forming an acoustical discontinuity in the middle of the array of some embodiments will have a minor, but insignificant effect on the TE mode transmission or reception beam pattern for that element. The small notch will be a non-active region for the TE mode resonance and therefore contribute to a "hole" in the very near field beam pattern for each element. The important beam characteristics however, such as the main lobe effective beam width and amplitude, will not be substantially affected, and except for a very minor rise in the transducer elevation side lobes, reasonable beam characteristics will be preserved as if the entire length of the transducer element was uniformly active.

Modal Dispersion

The TE mode transducer operation will exist with other resonant modes simultaneously. The efficiency of electromechanical energy coupling however for each mode though depends on primarily these factors: a) the k coefficient that describes the energy efficiency of transduction for a given resonance node, b) the acoustic coupling path to the desired insonification medium, and c) the echo transmission-reception signal bandwidth matching to the transducer resonance for that particular mode. Thus, for the creation of a "side looking" image, a transducer design is created to optimize the factors above for only the TE resonance, while the other resonant modes within a transducer are to be ignored through the design which suppresses the undesired resonances by minimizing the energy coupling factors mentioned above.

Through this frequency dispersion of unwanted coupling, the desired echoes transmitted and received from the "side looking" transducer port necessary to create a B-mode image plane will be most efficiently coupled through the TE resonance mode within any particular element. Therefore, the proposed transducer design which features a high efficiency TE mode coupling for desired echoes and frequency dispersion of the unwanted resonances and echoes, along with the other modal isolation reasons stated in an earlier section, constitutes a means for high quality TE echo energy transduction for only those desired in-plane echoes used in the creation of the B-mode cross-sectional image plane.

2. System operation for the Standard Cross-Sectional B-Mode Imaging

Figure 9:
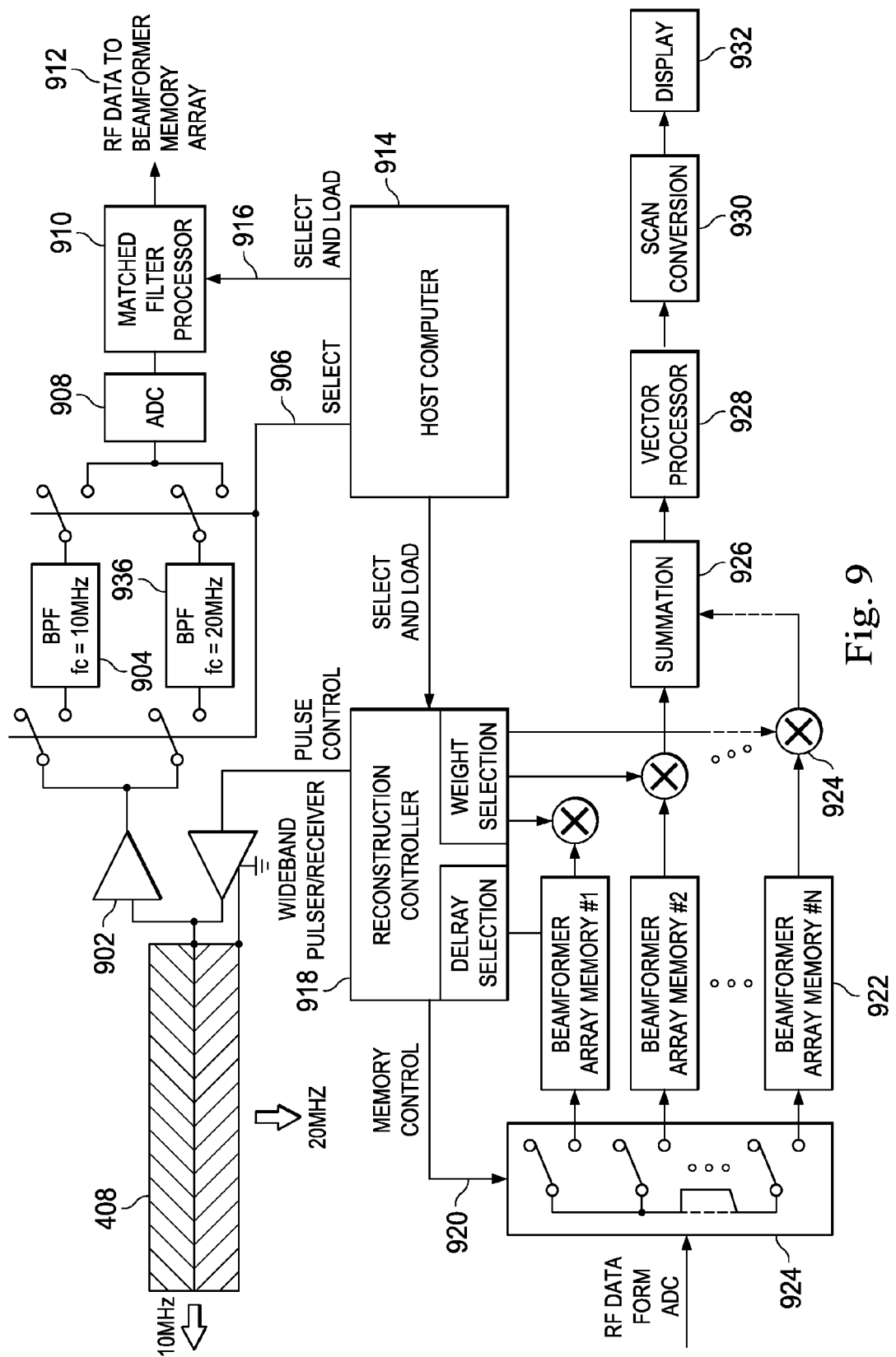
FIG. 9 is a diagrammatic, schematic view of an imaging system according to an embodiment of the present disclosure.

The host ultrasound processing system shown in FIG. 9 controls the ultrasound array 408 element selection and stepping process whereby a single element 412 or multiple elements will transmit and the same or other elements will receive the return echo information. The elements in the array that participate in a given aperture will be sampled sequentially so that all essential cross product transmit-receive terms needed in the beam forming sum are obtained.

The host processing system or computer 914 and reconstruction controller 918 will control the transmit pulse timing provided to wideband pulser/receiver 902, the use of any matched filter 910 via control line 916 to perform echo pulse compression. The echo band pass filter (BPF) processing paths in the system are selected using control signal 906 to select between either the 10 MHz 904 or 20 MHz 936 center frequency BPF paths. The amplified and processed analog echo information is digitized using ADC 908 with enough bits to preserve the dynamic range of the echo signals, and passed to the beam-former processing section via signal 912. The beam former section under the control of reconstruction controller 918 uses stored echo data from all the transmit-receive element pairs that exist in an aperture of interest. As the element echo sampling continues sequentially around the circular array, all element group apertures are "reconstructed" using well known synthetic aperture reconstruction techniques to form beam-formed vectors of weighted and summed echo data that radially emanate from the catheter surface using beam-former memory array 922, devices 924 and summation unit 926. Memory control signal 920 controls switch bank 924 which selects which memory array to store the incoming data.

The vector echo data is processed through envelope detection of the echo data and rejection of the RF carrier using vector processor 928. Finally a process of coordinate conversion is done to map the radial vector lines of echo data to raster scan data using scan converter 930 for video display using display 932.

This processing system, through the host control, may also accomplish blood velocity detection by tracking the blood cells through the elevation length of the transducer beams. The tracking scheme involves a modification of the element echo sampling sequencing and the use of the beam-former section of the host processing system. The blood velocity information may be displayed as a color on the video display; this blood velocity color information is superimposed on the image display to allow the user to see simultaneous anatomical information and blood movement information.

Forward Looking Cross-Sectional C-Mode Operation

The advantage of this "forward looking" operation of the catheter imaging device is in its ability to see an image of objects in front of the catheter where possibly the catheter could not otherwise physically traverse. A "forward" C-mode plane produces a cross-sectional view similar to the standard B-mode cross-sectional view, and so can offer comparable image interpretation for the user, and as well this forward image plane is made more useful because the user can see the presence of image targets at the center of the image, otherwise obscured in the standard cross-sectional view by the catheter itself. This forward view allows also the ideal acoustic beam positioning for the detection and color image display of Doppler echo signals from targets moving generally in parallel with the long axis of the catheter device.

1. Transducer Operation

The transducer in this "secondary" mode operates in the length extensional (LE) resonance, utilizing the $k_{31}$ electromechanical coupling coefficient to describe the coupling efficiency. In this mode of operation, the poling direction of the transducer element and the sensed or applied electric field in the transducer are in alignment, but the acoustic resonance is at 90 degrees to the electric field and poling direction. This "length resonance" refers fundamentally to a half wave resonance in the transducer element's length dimension that is at 90 degrees with the polarization direction of the transducer. The LE mode of resonance, which is typically much lower in resonant frequency than the TE mode because the element length is normally much longer than the thickness dimension, always exists to some extent in a typical transducer array element, but is usually suppressed through a frequency dispersive design.

Some embodiments of the present disclosure utilize an abrupt physical discontinuity (a notch) in the transducer element to allow a half wave LE resonance to manifest itself at a desired frequency, in the case of the preferred embodiment, at about one half the frequency of the TE mode resonance. A unique feature of this disclosure is a mechanically fixed transducer design that allows two resonant modes to operate at reasonably high efficiencies, while the "selection" of a desired mode (i.e. "side", or "forward") is a function of a) an electronically selected frequency band of interest, b) a transducer design that spatially isolates the echo beam patterns between the two modes, and c) image plane specific beam-forming weights and delays for a particular desired image plane to reconstruct using synthetic aperture beam-forming techniques, where echo timing incoherence between the "side" and "forward" beam patterns will help maintain modal isolation.

As discussed earlier, a resonant mode in a transducer design can be made efficient in electromechanical energy coupling if at least the three fundamental factors effecting coupling merit are optimized, namely a) the k coefficient (in this case it is the $k_{31}$ electro-mechanical coupling coefficient) that describes the energy efficiency of transduction for a given resonance node, b) the acoustic coupling path to the desired insonification medium, and c) the echo transmission-reception signal bandwidth matching to the transducer resonance for that particular mode. The disclosure allows for reasonable optimization of these factors for the LE mode of resonance, although the LE mode coupling efficiency is lower than that of the TE mode coupling. The $k_{31}$ coupling factor, used in describing LE mode efficiency, is typically one half that of $k_{33}$, the coupling factor that describes the TE mode efficiency.

The abrupt acoustical discontinuity in the transducer element is created at a step in the assembly of the array. Following the attachment of the transducer material to the flex circuit to create a mechanical bond and electrical connection between the transducer block and the flex circuit, while the transducer material is still in block form, a dicing saw cut can be made the entire length of the transducer material block, creating the notch. The notch depth should be deep enough in the transducer material to create an abrupt discontinuity in the distal portion of the transducer material to allow for a high efficiency LE mode half wave resonance to exist in this end of the transducer element. The saw cut should not be so deep as to sever the ground electrode trace on the transducer block side bonded to the flex circuit. The cut should ideally have a taper on the proximal side to allow for acoustically emitted energy to be reflected up into the backing material area and become absorbed.

Generally, it is not desirable to have any acoustic coupling exist between the LE modes of resonance in the distal and proximal transducer regions separated by the notch. The distal transducer region LE mode half wave resonance will exist at 10 MHz in PZT (Motorola 3203HD) for a length of about 170 microns between the distal end of the transducer element and the notch. The proximal transducer region LE mode resonance will exist at a frequency considered out of band (approximately 6 MHz) in the two embodiments shown in FIGS. 5 and 7 so as to minimally interfere with the desired operating frequencies (in this case 10 MHz LE mode resonance in the distal region for "forward" acoustic propagation, and 20 MHz TE mode resonance in the entire active field length of the transducer).

The desired acoustic energy coupling port of the distal transducer LE resonant mode region is at the distal end of the catheter array. To protect the end of the array and potentially act as an acoustic matching layer, an end cap made of polyurethane could be used, or alternatively, a uniform coating of adhesive material would suffice. The beam pattern produced by this acoustic port must be broad enough to insonify a large area that covers intended extent of the image plane to be formed. To this end, the beam pattern must typically be at least 60 degrees wide as a "cone shaped" beam measured in the plane to be formed at the half-maximum intensity angles for 2-way (transmitted and received) echoes. The preferred design of the array has 64 or more elements, and a transducer sawing pitch equal to pi times the catheter array diameter divided by the number of elements in the array. For an effective array diameter of 1.13 mm and 64 elements, the pitch is 0.055 mm. Using two consecutive array elements as a "single" effective LE mode acoustic port can provide an adequate, uniform beam pattern that produces the required 60-degree full-width half maximum ("FWHM") figure of merit. The aperture of this "single" forward looking port is then approximately 0.080 mm by 0.085 mm (where 0.085 mm is twice the pitch dimension minus the kerf width of 0.025 mm).

The transducer design may also include a version where no notch is needed in the transducer block. In this case, the driven electrode can exist all along one surface of the transducer element, and the ground or reference electrode can exist all along the opposite side of the element. The long axis length of the transducer will resonate at a half wavelength in LE mode, and the thickness dimension will allow the production of a TE mode resonance in that thickness dimension. In order for this design to operate though, the LE and TE mode resonant frequencies will be quite different in order to maintain the proper TE mode elevation beam focus. As an example, in maintaining the length of the active region of the element for an adequately narrow 20 MHz TE mode elevation beam width at 3 mm radially distant from the catheter, the element length should be approximately 0.5 mm long. The resulting half wave resonance frequency in LE mode then will be about 3 MHz. This design can be used for dual-mode imaging, but will not offer the focusing benefits that 10 MHz imaging can offer for the forward looking image planes. Other designs are possible, where the forward frequency is maintained near 10 MHz, but the required frequency for the side-looking mode will rise dramatically, and although this can be useful in itself, will complicate the design by requiring a concomitant increase in the number of elements and/or a reduction in the array element pitch dimension.

2. System Operation

The host processing system will control the array element selection and stepping process whereby one element, a two element pair, or other multiple elements in combination, will transmit and the same or other elements will receive the return echo information. The intended array operational mode is the LE resonant mode to send and receive echo information in a forward direction from the end of the catheter array. As stated earlier, the LE mode echoes produced may be isolated from the TE mode echoes through primarily frequency band limitations (both by transducer structural design and by electrical band selection filters), and through the beam-forming reconstruction process itself as a kind of echo selection filter.

To produce an image of the best possible in-plane resolution while operating in the forward-looking cross-sectional C-mode, the entire array diameter will be used as the maximum aperture dimension. This means that, in general, element echo sampling will take place at element locations throughout the whole array in preferably a sparse sampling mode of operation to gather the necessary minimum number of cross-product echoes needed to create image resolution of high quality everywhere in the reconstructed plane.

By using transmit-receive echo contributions collected from elements throughout the whole catheter array, using either a "complete data set" (e.g. 64×32), or a sparse sampling (e.g. less than 64×32) of elements, the FWHM main beam resolution will be close to the 20 MHz resolution of the "side looking" cross-sectional image. This is due to the fact that although the "forward looking" echo frequency is about one half as much as the "side looking" frequency, the usable aperture for the forward looking mode is about 1.6 times that of the largest side looking aperture (i.e. the largest side looking aperture is about 0.7 mm, and the forward aperture is about 1.15 mm). For a 10 MHz forward looking design, the FWHM main lobe resolution in an image plane reconstructed at a depth of 3 mm will be approximately 0.39 mm, and 0.65 mm resolution at 5 mm distance.

Due to the limitation of beam diffraction available in the design using 10 MHz as the echo frequency for "forward looking", the C-mode image diameter that can be reconstructed and displayed with a high level of resolution from echo contributions throughout the whole array will be related to the distance between the reconstructed C-mode image plane and the distal end of the catheter. At 3 mm from the end of the catheter, the C-mode image diameter will be about 2.3 mm, at 5 mm distance the image diameter will be 4.6 mm, and at 7 mm distance the image diameter will be 6.9 mm.

The host processing system, in addition to the control of the transducer element selection and stepping around the array, will control the transmit pulse timing, the use of any matched filter to perform echo pulse compression, and the echo band pass filter processing path in the system. The amplified and processed analog echo information is digitized with enough bits to preserve the dynamic range of the echo signals, and passed to the beam-former processing section. The beam former section uses stored echo data from the sparse array sampling (or alternatively the whole complete array echo data set of 64.times.32 of transmit-receive element pairs) that exist in an aperture of interest. As the element echo sampling continues sequentially around the circular array 1108 as shown in FIGS. 10 and 11, a number of "full trips" around the array will have been made to collect a sufficient number of echo cross-products (up to 105 in the preferred sparse sampling method) to allow the reconstruction of one image vector line 1102. As cross-product sampling continues around the array, the "older" echo cross-product collections are replaced with new samples and the next image vector is formed. This process repeats through an angular rotation to create new image vectors while sampling their element cross-product contributors around the array. In the same manner as described in the processing of the "side looking" image, the vector echo data is processed through envelope detection of the echo data and rejection of the RF carrier. Finally a process of coordinate conversion is done to map the radial vector lines of echo data to raster scan data for video display.

This processing system, through the host control, may also accomplish "forward looking" target (such as blood cells) velocity detection by either correlation-tracking the targets along the "forward looking" direction (with processing as earlier discussed with the "side looking" approach), or by standard Doppler processing of echo frequency shifts that correspond to target movement in directions parallel with the "forward looking" echo paths. The target (e.g. blood) velocity information may be displayed as a color on the video display; this velocity color information is superimposed on the image display to allow the user to see simultaneous anatomical information and target movement information.

Forward Looking Sagittal-Sectional B-Mode Operation

The advantage of the "forward looking" operation of the catheter imaging device is in its ability to see an image of objects in front of the catheter where possibly the catheter could not otherwise physically traverse. "Forward" B-mode plane imaging produces a cross-sectional planar "sector" view (see FIG. 8) that can exist in any plane parallel to the catheter central axis and distal to the end of the catheter array. This imaging mode may be used, in addition, to produce image "sector" views that are tilted slightly out of plane (see FIG. 8), and as well, may produce individual or sets of image "sectors" rotated generally about the catheter axis to allow the user to see a multitude of forward image slices in a format that shows clearly the multidimensional aspects of the forward target region of interest. This forward B-mode imaging (as with C-mode plane imaging) utilizes the ideal acoustic beam positioning for the detection and color image display of Doppler echo signals from targets moving generally in parallel with the long axis of the catheter device.

1. Transducer Operation

The transducer operation in creating the "forward looking" B-mode image format is virtually the same as discussed earlier for creating the "forward looking" C-mode image. The transducer in this "secondary" mode operates in the length extensional (LE) resonance, utilizing the $k_{31}$ electromechanical coupling coefficient to describe the coupling efficiency. As with the C-mode image creation, the number of elements used at any time to form a wide beam pointing in the "forward" direction are selected to produce a required 60 degree FWHM beam width performance; the modal isolation techniques mentioned earlier against the higher frequency TE resonances are valid as well for this forward B-mode imaging method.

However, where it is merely preferred to operate the "forward" C-mode imaging with high bandwidth echo signals (low bandwidth echo signals can also be used, but with some minor loss in image resolution), it is a requirement in the "forward" B-mode imaging that only high bandwidth echo signals (echo fractional bandwidth greater than 30%) be used to preserve the "axial" resolution in the "forward" B-mode image. The lateral resolution in the "forward" B-mode image is determined (as the C-mode image plane resolution) by the aperture (diameter of the array) used for the image reconstruction. The lateral resolution performance will be as stated earlier (i.e. from the description of the C-mode imaging case) for various depths from the catheter distal end.

2. System Operation

The system operation in creating the "forward looking" B-mode image format is largely the same as discussed earlier for creating the "forward looking" C-mode image, with the difference being in the use of the echo signals collected in the beam-forming process to create, rather than a C-mode image plane, a "forward" sagittal B-mode image in a plane that effectively cuts through the center of the circular array at the distal end of the catheter.

The host processing system, as shown in FIG. 9, will control the array element selection and stepping process whereby one element, a two element pair, or other multiple elements in combination, will transmit and the same or other elements will receive the return echo information. The intended array operational mode is the LE resonant mode to send and receive echo information in a forward direction from the end of the catheter array. As stated earlier, the LE mode echoes produced may be isolated from the TE mode echoes through primarily frequency band limitations (both by transducer structural design and by electrical band selection filters), and through the beam-forming reconstruction process itself as a kind of echo selection filter.

To produce an image of the best possible in-plane resolution while operating in the "forward looking" sagittal B-mode, the entire array diameter will be used as the maximum aperture dimension. This means that, in general, element echo sampling will take place at element locations throughout the whole array in preferably a sparse sampling mode of operation to gather the necessary minimum number of cross-product echoes needed to create image resolution of high quality everywhere in the reconstructed plane. By using transmit-receive echo contributions collected from elements throughout the whole catheter array, using either a "complete data set" (e.g. 64×32), or a sparse sampling (e.g. less than 64×32) of elements, the FWHM main beam lateral resolution in the B-mode plane will be close to the 20 MHz resolution of the "side looking" cross-sectional image. Similarly, as stated earlier for the C-mode image case, in the creation of the B-mode image using a 10 MHz forward looking design, the FWHM main lobe lateral resolution in the image plane reconstructed at a depth of 3 mm will be approximately 0.39 mm, and 0.65 mm resolution at 5 mm distance.

Due to the limitation of beam diffraction available in the design using 10 MHz as the echo frequency for "forward looking", the B-mode sector image width that can be reconstructed and displayed with a high level of resolution from echo contributions throughout the whole array will be related to the distance between the reconstructed B-mode target depth in the image sector and the distal end of the catheter. At 3 mm from the end of the catheter, the B-mode image sector width will be about 2.3 mm, at 5 mm distance the image sector width will be 4.6 mm, and at 7 mm distance the image sector width will be 6.9 mm.

The host processing system, in addition to the control of the transducer element selection and stepping around the array, will control the transmit pulse timing, the use of any matched filter to perform echo pulse compression, and the echo band pass filter processing path in the system. The amplified and processed analog echo information is digitized with enough bits to preserve the dynamic range of the echo signals, and passed to the beam-former processing section. The beam former section uses stored echo data from the sparse array sampling (or alternatively the whole complete array echo data-set of 64.times.32 of transmit-receive element pairs) that exist in an aperture of interest. As the element echo sampling continues sequentially around the circular array, a number of "full trips" around the array will have been made to collect a sufficient number of echo cross-products (up to 105 in the preferred sparse sampling method) to allow the reconstruction of one image vector line. As cross-product sampling continues around the array, the "older" echo cross-product collections are replaced with new samples and the next image vector is formed. This process repeats through an angular rotation in the array to create new image vectors while sampling their element cross-product contributors around the array.

The method used for the creation of a single "forward looking" sagittal B-mode image plane may be expanded to create multiple rotated sagittal planes around an axis either congruent with the catheter central axis, or itself slightly tilted off the catheter central axis. If enough rotated planes are collected, the beam-forming system could then possess a capability to construct and display arbitrary oblique "slices" through this multidimensional volume, with B-mode or C-mode visualization in either a 2-D sector format, a 2-D circular format, or, other multidimensional formats. The echo data volume may also be off-loaded to a conventional 3-D graphics engine that could create the desired image format and feature rendering that would enable improved visualization. In the same manner as described in the processing of the "forward looking" C-mode image, the vector echo data is processed through envelope detection of the echo data and rejection of the RF carrier. Finally a process of coordinate conversion is done to map the radial vector lines of echo data to a video sector-format display of the "forward looking" B-mode image.

This processing system, through the host control, may also accomplish "forward looking" target (such as blood cells) velocity detection by either correlation-tracking the targets along the "forward looking" direction (with processing as earlier discussed with the "side looking" approach), or by standard Doppler processing of echo frequency shifts that correspond to target movement in directions parallel with the "forward looking" echo paths in the "forward looking" B-mode plane. The target (e.g. blood) velocity information may be displayed as a color on the video display; this velocity color information is superimposed on the image display to allow the user to see simultaneous anatomical information and target movement information.

The disclosure has a number of important features and advantages. It provides an ultrasonic imaging transducer and method that can be used for imaging tissue in multiple planes without any moving parts. It can operate in both forward and side imaging modes, and it permits imaging to be done while procedures are being carried out. Thus, for example, it can operate in a forward looking C-mode, while at the same time a therapeutic device such as a laser fiber-bundle can be used to treat tissue (e.g. an uncrossable arterial occlusion) ahead of the catheter tip either by tissue ablation, or, tissue photo-chemotherapy. The laser pulses may be timed with the ultrasound transmit-receive process so that the high frequency laser induced tissue reverberations can be seen in the ultrasound image plane simultaneously. In this way the disclosure can dynamically guide the operator's vision during a micro-surgical procedure.

In some instances, the present disclosure is directed to a method of crossing a severe occlusion of a vessel of a patient. In that regard, the method includes introducing a flexible, elongate imaging device into the vessel of the patient, advancing the imaging device to a position immediately adjacent the severe occlusion of the vessel such that a tapered distal tip of the imaging device is in contact with the occlusion and such that at least one imaging element of the imaging device is spaced from the occlusion by a distance less than 5 mm, less than 3 mm, or less than 1 mm; and obtaining images of the vessel, including the occlusion, with the imaging device positioned immediately adjacent the severe occlusion. In some instances, the imaging device is an ultrasound device and the at least one imaging element is an ultrasound transducer. In other instances, the imaging device is an optical coherence tomography device and the at least one imaging element is an optical fiber or a reflector. Further, in some embodiments flexible, elongate imaging device is a catheter, such as a rapid-exchange catheter or an over-the-wire catheter. The method also includes penetrating the severe occlusion based on the images obtained by the imaging device. In that regard, penetrating the severe occlusion includes advancing an occlusion crossing device through a central lumen of the catheter to the occlusion. The occlusion crossing device may be one or more of an ablation device and a puncture device. In some instances, penetrating the severe occlusion comprises partially crossing the severe occlusion such that a recess is created in the occlusion, and the method further includes advancing the imaging device into the recess created by the partial crossing; obtaining images of the vessel, including the partially crossed occlusion, with the imaging device positioned within the recess; and further penetrating the severe occlusion based on the images obtained by the imaging device while positioned within the recess. This process can be repeated until the occlusion has been completely crossed. Further, in some instances, after the occlusion has been crossed a balloon or other expansion mechanism may be introduced into the opening created through the occlusion and used to further expand the opening. In some instances, the balloon or other expansion mechanism is attached to or formed as part of the imaging device.

In some embodiments, an imaging device for use in imaging a severe occlusion of a vessel of a patient is provided. The device includes an flexible elongate body having proximal portion and a distal portion, the flexible elongate body having a constant diameter along a majority of its length between the proximal and distal portions, the distal portion defining a distal tip that tapers from the constant diameter of the flexible elongate body to a smaller diameter as the distal tip extends distally along a longitudinal axis of the flexible elongate body, wherein the tapered portion of the distal tip has a length less than 5 mm as measured along the longitudinal axis of the flexible elongate body, and wherein at least the distal portion of the flexible elongate body includes a lumen extending along its length; and at least one imaging element secured to the distal portion of the flexible elongate body proximal of the tapered portion of the distal tip such that the at least one imaging element is spaced from a distal end of the flexible elongate body by a distance of 5 mm or less. In some embodiments, the imaging device is an ultrasound device and the at least one imaging element is an ultrasound transducer, such as single ultrasound transducer or an array of ultrasound transducer elements. In other embodiments, the imaging device is an optical coherence tomography device and the at least one imaging element is an optical fiber or a reflector. In some instances, the lumen is in communication with an opening in a sidewall of the flexible elongate body such that the imaging device is configured as a rapid-exchange catheter. In some instances, the lumen extends along a full length of the flexible elongate body such that the imaging device is configured as an over-the-wire catheter.

Aspects of the present disclosure can also be used in a biopsy or atherectomy procedure to allow the operator to perform a tissue identification prior to tissue excision; the advantage being that the catheter or biopsy probe device can be pointing in the general direction of the target tissue and thus aid significantly in the stereotaxic orientation necessary to excise the proper tissue sample. The disclosure can also be used for the proper positioning of a radiotherapy core wire in the treatment of target tissue that exists well beyond the distal extent of the catheter.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A method of crossing a severe occlusion of a vessel of a patient, the method comprising:
    introducing a flexible, elongate imaging device into the vessel of the patient, the imaging device including an array of imaging elements fixedly secured in an annular configuration around a distal portion of the imaging device, the distal portion of the imaging device terminating at a tapered distal tip, and a coaxial lumen extending longitudinally along the length of the imaging device and through the tapered distal tip such that the coaxial lumen defines an opening in the tapered distal tip, the coaxial lumen receiving an occlusion crossing device such that the occlusion crossing device selectively and coaxially extends beyond a distal most end of the tapered distal tip through the opening in the tapered distal tip, wherein the array of imaging elements is positioned less than 5 mm from the distal most end of the tapered distal tip;
    advancing the imaging device within the vessel such that the tapered distal tip is in contact with the severe occlusion and such that the array of imaging elements is spaced longitudinally from the occlusion by a distance less than 5 mm; and
    obtaining images of the vessel, including the occlusion, with the imaging device positioned immediately adjacent the severe occlusion.

2. The method of claim 1, wherein introducing a flexible, elongate imaging device into the vessel of the patient includes introducing an ultrasound device into the vessel of the patient, the ultrasound device including an array of ultrasound transducers.

3. The method of claim 1, wherein introducing a flexible, elongate imaging device into the vessel of the patient includes introducing a catheter into the vessel of the patient.

4. The method of claim 3, introducing a catheter into the vessel of the patient includes introducing a rapid-exchange catheter into the vessel of the patient.

5. The method of claim 3, wherein introducing a catheter into the vessel of the patient includes introducing an over-the-wire catheter into the vessel of the patient.

6. The method of claim 3, further comprising penetrating the severe occlusion based on the images obtained by the imaging device.

7. The method of claim 6, wherein penetrating the severe occlusion includes advancing the occlusion crossing device through the coaxial lumen of the catheter to the occlusion.

8. The method of claim 7, wherein the step of advancing the occlusion crossing device through the coaxial lumen of the catheter to the occlusion includes advancing an ablation device through the coaxial lumen of the catheter to the occlusion.

9. The method of claim 8, wherein the step of advancing the occlusion crossing device through the coaxial lumen of the catheter to the occlusion includes advancing a puncture device through the coaxial lumen of the catheter to the occlusion.

10. The method of claim 8, wherein penetrating the severe occlusion comprises partially crossing the severe occlusion such that a recess is created in the occlusion, and further comprising:
    advancing the imaging device into the recess created by the partial crossing;
    obtaining images of the vessel, including the partially crossed occlusion, with the imaging device positioned within the recess; and
    further penetrating the severe occlusion based on the images obtained by the imaging device while positioned within the recess.

11. The method of claim 10, wherein further penetrating the severe occlusion comprises a complete crossing of the occlusion.

12. The method of claim 1, wherein the step of advancing the imaging device to a position immediately adjacent the severe occlusion of the vessel includes advancing the imaging device such that the array of imaging elements of the imaging device is spaced from the occlusion by a distance less than 3 mm.

13. The method of claim 1, wherein the step of advancing the imaging device to a position immediately adjacent the severe occlusion of the vessel includes advancing the imaging device such that the array of imaging elements of the imaging device is spaced from the occlusion by a distance less than 1 mm.

14. The method of claim 1, wherein the step of obtaining images of the vessel further includes generating images using the array of imaging elements configured for side-looking imaging, the images being of a plane perpendicular to a longitudinal axis of the imaging device and passing through the array of imaging elements.

15. The method of claim 1, wherein the step of obtaining images of the vessel further includes generating images using the array of imaging elements configured for forward-looking imaging, the images being of a plane perpendicular to a longitudinal axis of the imaging device and spaced distally from the array of imaging elements.

16. The method of claim 1, wherein the step of obtaining images of the vessel further includes generating images using the array of imaging elements configured for forward-looking imaging, the images being of a plane parallel to a longitudinal axis of the imaging device and extending distally from the array of imaging elements.

17. An imaging device for use in imaging a severe occlusion of a vessel of a patient, the device comprising:

a flexible elongate body having proximal portion and a distal portion, the flexible elongate body having a constant diameter along a majority of its length between the proximal and distal portions, the distal portion defining a distal tip that tapers from the constant diameter of the flexible elongate body to a smaller diameter as the distal tip extends distally along a longitudinal axis of the flexible elongate body to a distal end of the flexible elongate body, wherein the tapered portion of the distal tip has a length less than 5 mm as measured along the longitudinal axis of the flexible elongate body, and wherein at least the distal portion of the flexible elongate body includes a coaxial lumen extending along its length for receiving an occlusion crossing device, the coaxial lumen extending through the tapered portion of the distal tip to define an opening in the distal tip; and an array of ultrasound transducer elements fixedly secured to the distal portion of the flexible elongate body in an annular configuration proximal of the tapered portion of the distal tip such that the array of ultrasound transducer elements is disposed adjacent the tapered portion of the distal tip and positioned 5 mm or less from a distal most end of the distal tip.

18. The device of claim 17, wherein the coaxial lumen is in communication with an opening in a sidewall of the flexible elongate body such that the imaging device is configured as a rapid-exchange catheter.

19. The device of claim 17, wherein the coaxial lumen extends along a full length of the flexible elongate body such that the imaging device is configured as an over-the-wire catheter.

20. The device of claim 17, wherein the array of ultrasound transducer elements is configured for side-looking imaging.

21. The device of claim 17, wherein the array of ultrasound transducer elements is configured for forward-looking imaging.

22. An imaging device for use in imaging a severe occlusion of a vessel of a patient, the device comprising:

a flexible elongate body having proximal portion and a distal portion, the flexible elongate body having a constant diameter along a majority of its length between the proximal and distal portions, the distal portion defining a distal tip that tapers from the constant diameter of the flexible elongate body to a smaller diameter as the distal tip extends distally along a longitudinal axis of the flexible elongate body, wherein the tapered portion of the distal tip has a length less than 5 mm as measured along the longitudinal axis of the flexible elongate body, and wherein at least the distal portion of the flexible elongate body includes a lumen extending along its length and through the tapered portion of the distal tip such that the lumen defines an opening in the distal tip; and at least one imaging element secured to the distal portion of the flexible elongate body proximal of the tapered portion of the distal tip such that the at least one imaging element is positioned 5 mm or less from a distal most end of the distal tip;

wherein the imaging device is an ultrasound device and wherein the at least one imaging element is an ultrasound transducer;

wherein the at least one imaging element is an array of ultrasound transducer elements.

* * * * *